United States Patent [19]

Buchel et al.

[11] 4,098,894
[45] Jul. 4, 1978

[54] TRIPHENYL-1,2,3-TRIAZOLYL-(1)-METHANES, AND COMPOSITIONS AND METHODS FOR COMBATING FUNGI AND BACTERIA EMPLOYING THEM

[75] Inventors: Karl Heinz Büchel, Wuppertal; Heinrich Gold, Schildgen; Paul-Ernst Frohberger; Helmut Kaspers, both of Leverkusen, all of Germany

[73] Assignee: Bayer Aktiengesellschaft, Leverkusen, Germany

[21] Appl. No.: 547,428

[22] Filed: Feb. 5, 1975

[30] Foreign Application Priority Data

Feb. 15, 1974 [DE] Fed. Rep. of Germany ....... 2407305

[51] Int. Cl.² .................... C07D 249/04; A01N 9/22
[52] U.S. Cl. ................................. 424/269; 260/308A
[58] Field of Search ...................... 260/308 A, 308 R; 424/269

[56] References Cited

U.S. PATENT DOCUMENTS 3,682,950   8/1972   Buchel et al. .................... 260/308 R

FOREIGN PATENT DOCUMENTS 1,940,626   2/1971   Fed. Rep. of Germany.
1,940,627   2/1971   Fed. Rep. of Germany.
1,940,628   2/1971   Fed. Rep. of Germany.

OTHER PUBLICATIONS

Gold, Chemical Abstracts, vol. 64, 2082g (1966).

*Primary Examiner*—Donald G. Daus
*Assistant Examiner*—Diana G. Rivers
*Attorney, Agent, or Firm*—Burgess, Dinklage & Sprung

[57] ABSTRACT

Triphenyl-1,2,3-triazolyl-(1)-methanes of the formula

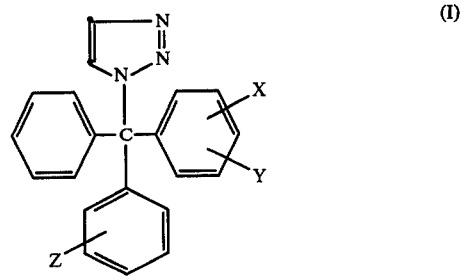

in which
  X and Z each independently is hydrogen, alkyl, halogen, nitrile or thiocyano, and
  Y is hydrogen, halogen, alkyl, halogenoalkyl or nitro,
which possess fungicidal and bactericidal properties.

13 Claims, No Drawings

TRIPHENYL-1,2,3-TRIAZOLYL-(1)-METHANES, AND COMPOSITIONS AND METHODS FOR COMBATING FUNGI AND BACTERIA EMPLOYING THEM

The present invention relates to and has for its objects the provision of particular new triphenyl-1,2,3-triazolyl-(1)-methanes, i.e. triphenyl-1,2,3-triazolyl-(1)-methanes optionally substituted on one or two phenyl rings, which possess fungicidal and bactericidal properties, active compositions in the form of mixtures of such compounds with solid and liquid dispersible carrier vehicles, and methods for producing such compounds and for using such compounds in a new way especially for combating pests, e.g. fungi and bacteria, with other and further objects becoming apparent from a study of the within specification and accompanying examples.

It has been disclosed in German published specification DOS No. 1,795,249, that certain triphenyl-1,2,4-triazolyl-(1)-methanes, especially (3'-trifluoromethylphenyl)-bis-phenyl-1,2,4-triazolyl-(1)-methane (Compound A), display good fungicidal properties. However, this activity is not always entirely satisfactory, especially if low amounts and low concentrations are used. Furthermore, the toleration of the compound by plants is not always satisfactory.

The present invention provides, as new compounds, the triphenyl-1,2,3-triazolyl-(1)-methanes of the general formula

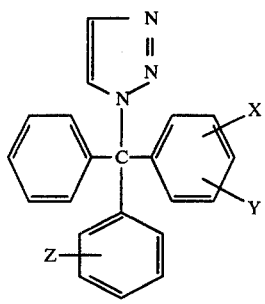

(I), in which
X and Z each independently is hydrogen, alkyl, halogen, nitrile or thiocyano, and
Y is hydrogen, halogen, alkyl, halogenoalkyl or nitro.

Preferably X and Y are each hydrogen, halogen, nitrile, or straight-chain or branched alkyl with up to 4 carbon atoms (especially methyl, ethyl, isopropyl or tertiary butyl), and Y is hydrogen, halogen (especially fluorine, chlorine or bromine), straight-chain or branched alkyl with 1 to 4 carbon atoms (especially methyl, ethyl or tertiary butyl), halogenoalkyl with 1 or 2 carbon atoms and 2 to 5 halogen atoms (especially fluorine and/or chlorine, as in, for example, trifluoromethyl and pentafluoroethyl), or nitro.

Surprisingly, the triphenyl-1,2,3-triazolyl-(1)-methanes according to the invention possess a better fungicidal activity, especially against species of mildew, than (3'-trifluoromethylphenyl)-bis-phenyl-1,2,4-triazolyl-(1)-methane, which is chemically the nearest active compound known from the state of the art. Furthermore, they are distinguished by better toleration by plants. They thus represent a genuine enrichment of the art.

The present invention also provides a process for the preparation of a triphenyl-1,2,3-triazolyl-(1')-methane of the formula (I), in which
(a) a trityl halide of the general formula

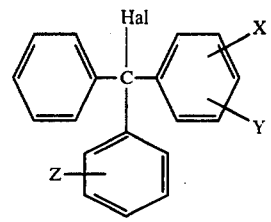

(II), in which
X, Y and Z have the above-mentioned meanings and
Hal is halogen, preferably chlorine or bromine, is reacted with 1,2,3-triazole, optionally in the presence of an acid-binding agent and of a solvent of diluent, at a temperature between about 60° and 150° C, or (b) a trityl azide of the general formula

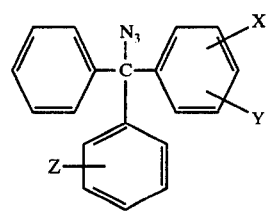

(III), in which
X, Y and Z have the above-mentioned meanings, is reacted with acetylene, optionally in the presence of a solvent, at a temperature between about 60° to 150° C.

If (3'-trifluoromethylphenyl)-bis-phenyl-methyl chloride and 1,2,3-triazole are used as starting materials in process variant (a), the course of the reaction is shown by the following equation:

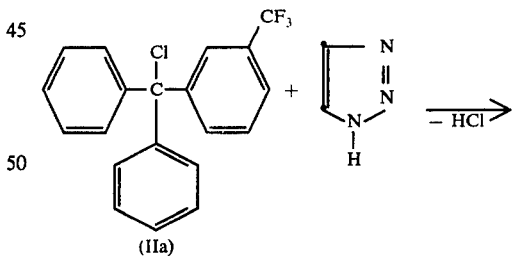

(IIa)

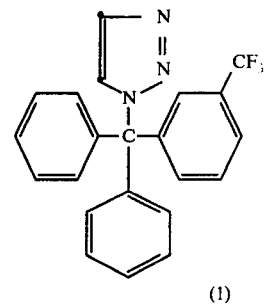

(I)

If (3'-trifluoromethylphenyl)-bis-phenyl-methyl azide and acetylene are used as starting materials in process variant (b), the course of the reaction can be represented by the following equation:

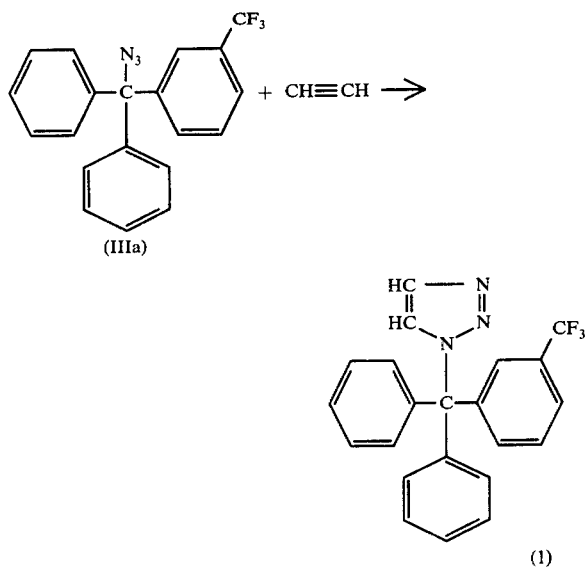

Trityl halides of the formula (II) used as starting materials are known and can be prepared according to customary methods, e.g. German published specification DOS Nos. 1,670,932, 1,795,249 and 1,670,976 and U.S. Pat. No. 3,321,366. The following may be mentioned as examples of the trityl halides of the formula (II) which can be used according to the invention: 2-fluorophenyl-bis-phenyl-methyl chloride, 2-cyanophenyl-bis-phenyl-methyl chloride, 3-nitrophenyl-bis-phenyl-methyl chloride, 3-methyl-phenyl-bis-phenyl-methyl chloride, 3,4-dichloro-phenyl-bis-phenyl-methyl chloride, 2-isopropylphenyl-bis-phenyl-methyl chloride, 3-bromophenyl-bis-phenyl-methyl chloride, 4-trifluoromethylphenyl-bis-phenyl-methyl chloride, 3-iodophenyl-bis-phenyl-methyl chloride, 2-chlorophenyl-bis-phenyl-methyl chloride, di-(2-chlorophenyl)-phenyl-methyl chloride, di-(4-chlorophenyl)-phenyl-methyl chloride, di-(2-methylphenyl)-phenyl-methyl chloride, di-(4-methyl-phenyl)-phenyl-methyl chloride, 2,3-dimethylphenyl-bis-phenyl-methyl chloride, 2,4-dimethylphenyl-bis-phenyl-methyl chloride, 2,5-dimethylphenyl-bis-phenyl-methyl chloride and 2,6-dimethylphenyl-bis-phenyl-methyl chloride.

Trityl azides of the formula (III) used as starting materials are disclosed in Beilstein's "Handbuch der organischen Chemie" ("Handbook of Organic Chemistry"), H 5, 708, E I 349, II 618, III 2323. They can be prepared in the usual manner, for example, by reacting trityl halides of the formula (II) with sodium azide, optionally in the presence of a polar solvent such as dimethylformamide, at temperatures of 50° to 100° C, preferably between 60° and 90° C, and isolating, and optionally purifying, the product in accordance with customary methods. Preferably, however, isolation of the azide is dispensed with and the reaction solution is immediately reacted further (see Examples 7a (ii) and 8b herein). The following may be mentioned as examples of the trityl azides of the formula (III) which can be used according to the invention: triphenylmethyl azide, 2-chlorophenyl-bis-phenyl-methyl azide and 3-trifluoromethylphenyl-bis-phenyl-methyl azide.

Diluents which can be used in process variant (a) are polar organic solvents, especially nitriles such as o- and p-toluinitrile and acetonitrile, ethers such as tetrahydrofuran and dioxane, sulfoxides such as dimethyl sulfoxide, and amides such as dimethylformamide or hexamethylphosphoric acid triamide.

Customary inorganic and organic acid acceptors can be used as acid-binding agents. The following may be mentioned as being preferred: alkali metal carbonates, such as potassium carbonate and sodium carbonate, alkaline earth metal carbonates, such as barium carbonate and magnesium carbonate, alkaline earth metal hydroxides, such as barium hydroxide and magnesium hydroxide, and tertiary organic bases, such as triethylamine or pyridine.

The reaction according to process variant (a) is preferably carried out at temperatures of between 80° and 120° C, and under normal pressure.

Preferably, 1 mole of 1,2,3-triazole and 1 mole of acid acceptor is employed per mole of trityl halide of the formula (II). However, an excess of 1,2,3-triazole, e.g. 2 to 2.3 moles can also be used as an acid acceptor. To isolate the active compounds, the solvent is distilled off and the residue is washed well with water to remove the halide formed and is purified by recrystallization if desired.

Possible diluents in process variant (b) are also polar organic solvents, especially ethers, such as tetrahydrofuran or dioxane; ketones, such as acetone or methyl ethyl ketone; amides such as dimethylformamide or hexamethylphosphoric acid triamide; and sulfoxides such as dimethylsulfoxide.

The reaction according to process variant (b) is also preferably carried out at temperatures of between about 80° and 120° C.

In general, the reaction is carried out at pressures of about 5 to 20 kg/cm², preferably at about 10 kg/cm².

Preferably, about 1 mole of acetylene is employed per mole of trityl azide of the formula (III). However, a larger excess of acetylene can also be used; in that case control by infrared spectrography is used to ascertain completion of the reaction.

The active compounds are isolated by cooling the reaction solution, if appropriate with addition of water, and filtering off the resulting precipitate. They can optionally be purified by recrystallization.

The salts of the compounds of the formula (I) can be obtained in a simple manner, in accordance with customary methods for forming salts, for example by dissolving the base in ether, for example diethyl ether, and adding the acid, for example hydrogen chloride. The salts can be isolated in a known manner, for example by filtration, and be purified if desired.

The compounds (I) may be used as such or in the form of salts, especially of physiologically tolerated acids. Examples of such acids are the hydrogen halide acids, for example, hydrobromic acid and, especially, hydrochloric acid, phosphoric acid, monofunctional and bifunctional carboxylic acids and hydroxycarboxylic acids, such as acetic acid, maleic acid, succinic acid, fumaric acid, tartaric acid, citric acid, salicylic acid, sorbic acid and lactic acid, and 1,5-naphthalene-disulfonic acid.

The active compounds according to the invention exhibit a powerful fungitoxic action. Their low toxicity to warm-blooded animals and their good toleration by higher plants permits their use as plant protection agents against fungal diseases. They do not harm crop plants in the concentrations required to combat the fungi. Fungitoxic agents are employed in plant protection for combating fungi from the most diverse classes of fungi, such as Archimycetes, Ascomycetes, Basidiomycetes and Fungi Imperfecti.

The active compounds according to the invention can be used against parasitic fungi on above-ground parts of plants, fungi causing tracheomycosis, which attack the plant through the soil, seed-borne fungi and fungi which inhabit the soil. They are particularly active against fungi which cause powdery mildew diseases. This group of fungi predominantly includes representatives from the family of the Erysiphaceae, the most important genera being Erysiphe, Unicinula (Oidium), Sphaerotheca and Podosphaera.

The following may be mentioned individually as important fungi: *Erysiphe graminis, Podosphaera leucotricha, Uncinula necator* and *Botrytis cinerea*.

It should be emphasised that the active compounds according to the invention not only display a protective action but are also curatively active, that is to say active when used after infection of the plant by fungal spores. The systemic action of the compounds should also be pointed out. Thus, it proves possible to protect plants against fungal attack if the active compound is supplied to the above-ground parts of the plant through the soil and the root.

In addition, the good bactericidal activity of the active compounds according to the invention, especially against *Xanthomonas oryzae*, should be mentioned.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methyl chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite; montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and bactericides, or nematocides, insecticides, acaricides or rodenticides, herbicides, fertilizers, growth-regulating agents etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–0.05%, preferably 0.0005–2%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi and bacteria, and more particularly methods of combating fungi, which comprises applying to at least one of correspondingly (a) such fungi, (b)

such bacteria, and (c) the corresponding habitat thereof, i.e. the locus to be protected, e.g. to a growing crop, to an area where a crop is to be grown or to a domestic animal, a correspondingly combative or toxic amount, i.e. a fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Shoot treatment test/powdery mildew of cereals/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier; then 975 parts by weight of water were added. The concentrate was diluted with water to the desired final concentration of the spray liquor.

To test for protective activity, a single-leaved young barley plants of the Amsel Variety were sprayed with the preparation of active compound until dew-moist. After drying, the barley plants were dusted with spores of *Erysiphe graminis var. hordei.*

After 6 days' dwell time of the plants at a temperature of 21°–22° C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower the degree of mildew infection.

The active compounds, active-compound concentrations in the spray liquor and degrees of infection can be seen from the table which follows:

Table 1

Shoot treatment test/powdery mildew of cereals/protective (leaf-destructive mycosis)

| Active compounds | Active-compound concentrations in the spray liquor in % by weight | Infection in % of the untreated control |
|---|---|---|
| untreated | — | 100.0 |
| (Known) (A) | 0.1 | 0.0 |
| | 0.05 | 0.0 |
| | 0.025 | 0.0 |
| | 0.01 | 16.3 |
| | 0.005 | 33.8 |

Table 1-continued

Shoot treatment test/powdery mildew of cereals/protective (leaf-destructive mycosis)

| Active compounds | Active-compound concentrations in the spray liquor in % by weight | Infection in % of the untreated control |
|---|---|---|
| (1) 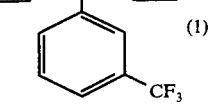 | 0.1 | 0.0 |
| | 0.05 | 0.0 |
| | 0.025 | 0.0 |
| | 0.01 | 0.0 |
| | 0.005 | 0.0 |

EXAMPLE 2

Shoot treatment test/powdery mildew of cereals/curative (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier; then 975 parts by weight of water were added. The concentrate was diluted with water to the desired final concentration of the spray liquor.

To test for curative activity the procedure followed was analogous to that for testing for protective activity, but in the converse sequence. The treatment of the single-leaved young barley plants with the preparation of active compound was carried out 48 hours after the inoculation, when the infection was already manifest.

After 6 days' dwell time of the plants at a temperature of 21°–22° C and 80–90% atmospheric humidity the occurrence of mildew postules on the plants was evaluated. The degree of infection is expressed as a percentage of the infection of the untreated control plants. 0% denotes no infection and 100% denotes the same degree of infection as in the case of the untreated control. The more active the compound, the lower the degree of mildew infection.

The active compounds, active-compound concentrations in the spray liquor and degrees of infection can be seen from the table which follows.

Table 2

Shoot treatment test/powdery mildew of cereals/curative (leaf-destructive mycosis)

| Active compound | Active-compound concentration in the spray liquor in % by weight | Infection in % of the untreated control |
|---|---|---|
| untreated | — | 100.0 |
| (known) (A) | 0.1 | 13.8 |
| | 0.05 | 13.8 |
| | 0.025 | 27.5 |
| | 0.01 | 27.5 |
| | 0.005 | 45.0 |

Table 2-continued

Shoot treatment test/powdery mildew of cereals/curative (leaf-destructive mycosis)

| Active compound | Active-compound concentration in the spray liquor in % by weight | Infection in % of the untreated control |
|---|---|---|
| (I) [structure: triazole with two phenyl groups and a 3-CF₃ phenyl group attached to central C] | 0.1<br>0.05<br>0.025<br>0.01<br>0.005 | 0.0<br>0.0<br>0.0<br>3.8<br>3.8 |

EXAMPLE 3

Botrytis test

Solvent: 4.7 parts by weight of acetone
Dispersing agent: 0.3 part by weight of alkylaryl polyglycol ether
Water: 95.0 parts by weight The amount of active compound required to give the desired concentration of active compound in the spray liquor was mixed with the stated amount of the solvent and the concentrate was diluted with the stated amount of water, which contained the stated additives.

Young (*Vicia faba*) bean plants of the Zwijndrechter variety, having 3-4 pairs of leaves, were sprayed with the spray liquor until dripping wet. After 24 hours, the pairs of leaves were removed and the individual leaves were placed in Petri dishes, the lid and bottom of which were lined with moist filter-paper discs. Filter-paper discs of 1 cm diameter were dipped into an aqueous spore suspension of *Botrytis cinerea* and placed on the treated leaves lying in the Petri dishes. After 48 hours' incubation at +20° C, the necroses visible under the discs were assessed.

0% denotes no infection and 100% denotes that the infection was exactly as great as in the case of the control plants.

The active compound, active-compound concentrations and results can be seen from the table which follows.

Table 3

Botrytis test

| Active compound | Infection in % of the infection of the untreated control at an active compound concentration of 0.005% |
|---|---|
| (known) (A) [structure: triazole linked to C bearing two phenyl groups and a 3-CF₃ phenyl group] | 54 |

Table 3-continued

Botrytis test

| Active compound | Infection in % of the infection of the untreated control at an active compound concentration of 0.005% |
|---|---|
| (I) [structure: triazole with two phenyl groups and a 3-CF₃ phenyl group attached to central C] | 21 |

EXAMPLE 4

Podosphaera test (powdery mildew of apples) [Protective]

Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were sprayed with the spray liquid until dripping wet. The plants remained in a greenhouse for 24 hours at 20° C and at a relative atmospheric humidity of 70%. They were then inoculated by dusting with conidia of the apple powdery mildew causative organism (*Podosphaera leucotricha* Salm.) and placed in a greenhouse at a temperature of 21°-23° C and at a relative atmospheric humidity of about 70%.

Ten days after the inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table:

Table 4

Podosphaera test/protective

| Active compound | Infection in % of the infection of the untreated control at an active-compound concentration of 0.00125% and 0.00062% | |
|---|---|---|
| (known) (A) [structure: triazole linked to C bearing two phenyl groups and a 3-CF₃ phenyl group] | 2 | 10 |

Table 4-continued

*Podosphaera* test/protective

| Active compound | Infection in % of the infection of the untreated control at an active-compound concentration of 0.00125% and 0.00062% |
|---|---|
| (1) [structure: N-vinyl-triazolyl-C(phenyl)₂-(3-CF₃-phenyl)] | 0    5 |

EXAMPLE 5

Phytotoxicity test/cucumbers

Solvent: 4.7 parts by weight of acetone
Emulsifier: 0.3 part by weight of alkylaryl polyglycol ether
Water: 95.0 parts by weight The amount of active compound required to give the desired concentration of active compound in the spray liquor was mixed with the stated amount of the solvent and the concentrate was diluted with the stated amount of water, which contained the stated additives.

Young cucumber plants were sprayed with the spray liquor until dripping wet. After drying, the plants were set up in a greenhouse at a temperature of +20° C and about 70% relative atmospheric humidity.

The plants were repeatedly assessed for damage. The period of observation was, as a rule, 10 days.

The assessment was carried out in accordance with a 1-9 rating scheme. 1 denotes no damage and 9 denotes that the plant was totally damaged or dead.

The active compounds, active-compound concentrations and results can be seen from the table which follows.

Table 5

Phytotoxicity test/cucumbers

| Active compound | Damage to cucumbers at an active-compound concentration of 0.05% |
|---|---|
| (known) (A) [structure shown] | 2.5 |
| (1) [structure shown] | 1.0 |

Substantially similar results can be obtained using the triphenyl-1,2,3-triazolyl-(1)-methanes in the form of their salts, e.g. the hydrochlorides.

The process of the present invention is illustrated by the following preparative Examples.

EXAMPLE 6

Process variant (a):

52.6 g (0.2 mole) of 3-trifluoromethylbenzotrichloride were slowly added dropwise at room temperature, while stirring, to a suspension of 32.4 g (0.2 mole) of iron(III) chloride in 300 ml of anhydrous benzene. After stirring for four hours, the reaction mixture was hydrolyzed with a mixture of ice and hydrochloric acid. The organic phase was separated off, dried over sodium sulfate, filtered and freed from the solvent in vacuo. The resulting (3'-trifluoromethylphenyl)-bis-phenylmethyl chloride (a light brown oil having a refractive index $n_D^{20}$ of 1.5728) was dissolved in 300 ml of anhydrous acetonitrile; 13.8 g (0.2 mole) of 1,2,3-triazole and 20.2 g (0.2 mole) of triethylamine were added and the mixture was heated to the boil for 3 hours. The solvent was then distilled off in vacuo and the residue was well washed with water and recrystallized from acetonitrile. 38 g (51% of theory) of (3'-trifluoromethylphenyl)-bis-phenyl-1,2,3-triazolyl-(1)-methane of melting point 124° C were obtained.

Process variant (b):

35 g (0.1 mole) of (3'-trifluoromethylphenyl)-bis-phenyl-methyl chloride were dissolved in 150 ml of dimethylformamide, 14 g (0.21 mole) of sodium azide were added to the solution and the mixture was stirred for 12 hours at 80° C. Thereafter, a further 8.5 g (0.16 mole) of sodium azide were added and the mixture was kept at 80° C for a further 8 hours. After filtering off the sodium chloride formed, the dimethylformamide solution was treated with a 2:1 mixture of acetylene nitrogen in an autoclave under 15 kg/cm² at 100° C. until the infrared spectrum of a sample no longer showed the band at 4.7μ which is attributable to the azide. At that stage the azide had been consumed. The reaction solution was then mixed with 150 ml of water. Hereupon, an oil first separated out, which soon solidified to crystals and was filtered off. These were recrystallized from 100 ml of methanol. 30.0 g (80% of theory) of (3'-trifluoromethyl-phenyl)-bis-phenyl-1,2,3-triazolyl-(1)-methane of melting point 122° C were obtained.

EXAMPLE 7

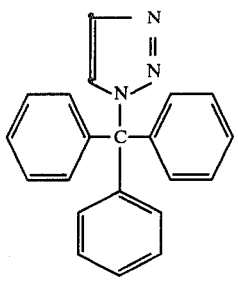
(2)

Starting material:

i. Triphenylmethyl azide was obtained by reaction of triphenylmethyl chloride with sodium azide in benzene at 80° C, in accordance with Example 1 of Berichte, Vol. 63 B (1930) pages 1176-1180. The following method was also used:

ii. 27.9 g (0.1 mole) of triphenylmethyl chloride were dissolved in 250 ml of dimethylformamide, 14 g (0.21 mole) of sodium azide were added to this solution and the mixture was stirred for 10 hours at 80° C. After this time, a further 8.5 g (0.16 mole) of sodium azide were added and the mixture was again stirred for 8 hours at 80° C. After filtering off the inorganic salt produced, there was left a dimethylformamide solution containing triphenylmethyl azide in approximately 80% yield.

iii. The dimethylformamide solution of triphenyl-methyl azide produced in (i) was immediately reacted further with acetylene, as described above. After cooling and recrystallization, 21.8 g of triphenyl-1,2,3-triazolyl-(1)-methane of the above-mentioned melting point were obtained; this corresponds to an overall yield of 70% based on triphenylmethyl chloride.

The synthesis of the final product has been accomplished as follows:

28.5 g (0.1 mole) of triphenylmethyl azide of melting point 64°-65° C were dissolved in 250 ml of acetone at 30° C. This solution was treated with a 2:1 mixture of acetylene and nitrogen in an autoclave under a pressurre of 15 atmospheres at 100° C until the infrared spectrum of a sample no longer showed the band at 4.7μ which is attributable to the azide. At that stage, the azide had been consumed. After cooling the reaction solution, a precipitate formed, which was filtered off and recrystallized from methyl ethyl ketone. 28 g (90% of theory) of triphenyl-1,2,3-triazolyl-(1)-methane of melting point 206°-207° C were obtained.

EXAMPLE 8

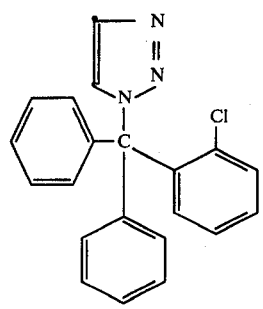
(3)

Following the description in Example 7 (process variant (b)), 2-chlorophenyl-bis-phenyl-methyl azide of melting point 97° C was dissolved in acetone and treated with an acetylene-nitrogen mixture in an autoclave at 100° C. After isolation and recrystallization from methyl ethyl ketone, (2'-chlorophenyl)-bis-phenyl-1,2,3-triazolyl-(1)-methane of melting point 164° C was obtained in approximately 68% yield.

This compound could also be prepared directly by reaction of 2-chlorophenyl-bis-phenyl-methyl chloride with sodium azide and acetylene, without isolation of the 2-chlorophenyl-bis-phenyl-methyl azide produced as an intermediate, in dimethylformamide as the solvent.

The compounds of the formula

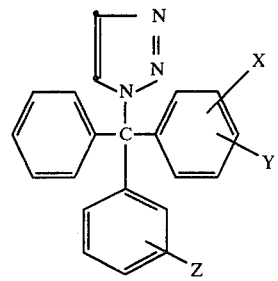
(I)

mentioned below were obtained analogously to the preceding examples:

| Compound No. | X | Y | Z | Melting point °C |
|---|---|---|---|---|
| 4 | 3-Cl | H | H | 119-121 |
| 5 | 4-Cl | H | H | 164-166 |
| 6 | 2-Cl | 4-Cl | H | 201-202 |
| 7 | 2-F | H | H | 178 |
| 8 | 2-CN | H | H | 129 |
| 9 | H | 3-NO$_2$ | H | 162 |
| 10 | 3-CH$_3$ | H | H | 138 |
| 11 | 4-Cl | H | 4-Cl | 119 |
| 12 | 3-Br | H | H | 143-144 |
| 13 | 4-CF$_3$ | H | H | 127 |
| 14 | 3-I | H | H | 107-109 |
| 15 | 2-CH(CH$_3$)$_2$ | H | H | 166-168 |
| 16 | H | 4-NO$_2$ | H | 130-132 |
| 17 | 2-CH$_3$ | H | H | 154-155 |

Other compounds which can be similarly obtained include:

(2'-methyl-4'-thiocyano-phenyl)-(4''-cyano-phenyl)-1,2,3-triazolyl-(1)-methane, (3'-bromo-4'-trifluoromethyl-phenyl)-(4''-ethylphenyl)-1,2,3-triazolyl-(1)-methane, (3′-fluoro-4″-pentafluoroethyl-phenyl)-(4″-thiocyanophenyl)-1,2,3-triazolyl-(1)-methane, and the like.

Any of the foregoing can be converted to their salts with acids as by addition of the acids, e.g. hydrochloric acid, to a solution of the triphenyl-1,2,3-triazolyl-(1)-methane in diethyl ether, followed by filtration.

It will be appreciated that the instant specification and examples are set forth by way of illustration and not limitation, and that various modifications and changes may be made without departing from the spirit and scope of the present invention.

What is claimed is:

1. A triphenyl-1,2,3-triazolyl-(1)-methane selected from the group consisting of (3′-trifluoromethylphenyl)-bis-phenyl-1,2,3-triazolyl-(1)-methane,
(3′-nitrophenyl)-bis-phenyl-1,2,3-triazolyl-(1)-methane,
(3′-bromophenyl)-bis-phenyl-1,2,3-triazolyl-(1)-methane,
(4′-trifluoromethylphenyl)-bis-phenyl-1,2,3-triazolyl-(1)-methane,
(3′-iodophenyl)-bis-phenyl-1,2,3-triazolyl-(1)-methane,
(2′-isopropylphenyl)-bis-phenyl-1,2,3triazolyl-(1)-methane, and
(4′-nitrophenyl)-bis-phenyl-1,2,3-triazolyl-(1)-methane.

2. A compound according to claim 1 wherein such compound is (3′-trifluoromethylphenyl)-bis-phenyl-1,2,3-triazolyl-(1)-methane of the formula

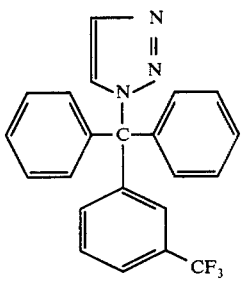

3. The compound according to claim 1, wherein such compound is (3′-nitrophenyl)-bis-phenyl-triazolyl-(1)-methane of the formula

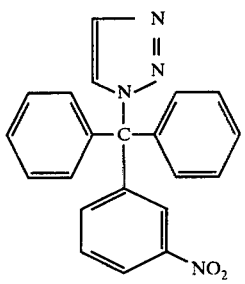

4. The compound according to claim 1, wherein such compound is (3′-bromophenyl)-bis-phenyl-triazolyl-(1)-methane of the formula

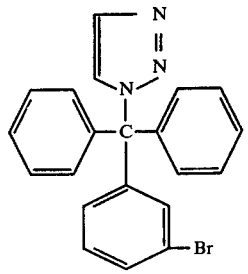

5. The compound according to claim 1, wherein such compound is (4′-trifluoromethylphenyl)-bis-phenyl-triazolyl-(1)-methane of the formula

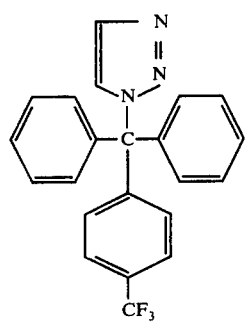

6. The compound according to claim 1, wherein such compound is (3′-iodophenyl)-bis-phenyl-1,2,3-triazolyl-(1)-methane of the formula

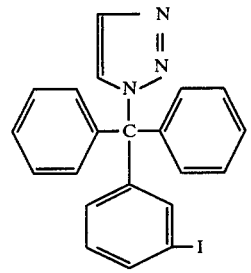

7. The compound according to claim 1, wherein such compound is (2′-isopropylphenyl)-bis-phenyl-1,2,3-triazolyl-(1)-methane of the formula

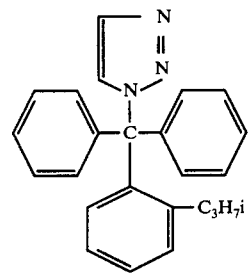

8. The compound according to claim 1, wherein such compound is (4′-nitrophenyl)-bis-phenyl-1,2,3-triazolyl-(1)-methane of the formula

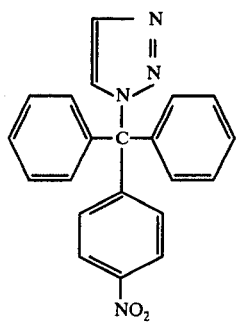

9. A compound according to claim 1 in the form of a salt with physiologically tolerated acids.

10. A composition for combating fungi and bacteria in agriculture, said composition containing as active ingredient a fungicidally or bactericidally effective amount of a compound according to claim 1 in admixture with a diluent.

11. A composition according to claim 10, wherein said compound is (3'-trifluoromethylphenyl)-bis-phenyl-1,2,3-triazolyl-(1)-methane.

12. A method of combating fungi or bacteria in agriculture which comprises applying to the fungi, bacteria or a habitat thereof a fungicidally or bactericidally effective amount of a compound according to claim 1.

13. A method according to claim 12, in which said compound is (3'-trifluoromethylphenyl)-bis-phenyl-1,2,3-triazolyl-(1)-methane.

* * * * *